(12) United States Patent
Sieben et al.

(10) Patent No.: US 11,906,501 B2
(45) Date of Patent: Feb. 20, 2024

(54) AUTOMATED METHOD AND APPARATUS FOR MEASURING SATURATE, AROMATIC, RESIN, AND ASPHALTENE FRACTIONS USING MICROFLUIDICS AND SPECTROSCOPY

(71) Applicant: Schlumberger Technology Corporation, Sugar Land, TX (US)

(72) Inventors: Vincent Joseph Sieben, Auburndale, MA (US); Farshid Mostowfi, Lexington, MA (US); Nejib Hamed, La Defense (FR); Alexander Stickel, Edmonton (CA); Collins Obiosa-Maife, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 17/346,560

(22) Filed: Jun. 14, 2021

(65) Prior Publication Data
US 2021/0302404 A1    Sep. 30, 2021

Related U.S. Application Data

(62) Division of application No. 15/579,271, filed as application No. PCT/US2015/034695 on Jun. 8, 2015, now Pat. No. 11,035,839.

(51) Int. Cl.
*G01N 33/28* (2006.01)
*G01N 1/38* (2006.01)
(Continued)

(52) U.S. Cl.
CPC ......... *G01N 33/2823* (2013.01); *E21B 49/08* (2013.01); *G01N 1/38* (2013.01);
(Continued)

(58) Field of Classification Search
CPC .. E21B 49/08; G01N 1/38; G01N 2001/4061; G01N 2030/027; G01N 21/05; G01N 21/31; G01N 33/28; G01N 33/2823
(Continued)

(56) References Cited

U.S. PATENT DOCUMENTS 4,298,472 A * 11/1981 Durand ............... B01J 20/3255
436/178
5,076,909 A    12/1991 Overfield et al.
(Continued)

FOREIGN PATENT DOCUMENTS

CA    2800879 A1    12/2011
CA    2757919 A1    5/2013
(Continued)

OTHER PUBLICATIONS

Aske, N. et al., "Determination of saturate, aromatic, resin, and asphaltenic (SARA) components in crude oils by means of infrared and near-infrared spectroscopy", Energy Fuels, 2001, 15(5), pp. 1304-1312.
(Continued)

*Primary Examiner* — Maureen Wallenhorst
(74) *Attorney, Agent, or Firm* — Ashley E. Brown

(57) ABSTRACT

A method of determining saturate, aromatic, resin, and asphaltene (SARA) fractions of a hydrocarbon fluid sample, including:
  i) microfluidic mixing that forms a mixture including the hydrocarbon fluid sample and a solvent fluid that dissolves asphaltenes;
  ii) performing optical spectroscopy on the hydrocarbon fluid sample-solvent fluid mixture resulting from i);
  iii) microfluidic mixing that forms a mixture including the hydrocarbon fluid sample and a titrant fluid that precipitates asphaltenes;
(Continued)

iv) microfluidically precipitating asphaltenes from the hydrocarbon fluid sample-titrant fluid mixture resulting from iii);
v) performing a microfluidic filtering operation that removes precipitated asphaltenes from the mixture resulting from iv) while outputting permeate;
vi) performing optical spectroscopy on the permeate resulting from v);
vii) determining an asphaltene fraction percentage of the hydrocarbon fluid sample based on the optical spectroscopy performed in ii) and vi);
viii) sequentially separating saturate-, aromatic-, and resin-containing portions from the permeate from v);
ix) for each separating of viii), measuring an optical property of the respective saturate-, aromatic-, and resin-containing portions over time; and
x) determining fraction percentages of saturates, aromatics, and resins in the hydrocarbon fluid sample based on the measured optical properties of ix) and respective mass-to-optical correlation data.

7 Claims, 9 Drawing Sheets

(51) Int. Cl.
  G01N 21/31 (2006.01)
  G01N 21/05 (2006.01)
  E21B 49/08 (2006.01)
  G01N 1/40 (2006.01)
  G01N 30/02 (2006.01)
(52) U.S. Cl.
  CPC ............ *G01N 21/05* (2013.01); *G01N 21/31* (2013.01); *G01N 2001/4061* (2013.01); *G01N 2030/027* (2013.01)
(58) Field of Classification Search
  USPC .................. 436/43, 60, 164, 174, 177, 180; 422/82.05, 82.09, 527, 534, 502–505
  See application file for complete search history.

(56) References Cited

U.S. PATENT DOCUMENTS

| | | |
|---|---|---|
| 8,269,961 B2 | 9/2012 | Mostowfi et al. |
| 8,530,240 B1 | 9/2013 | Schabron et al. |
| 8,584,513 B2 | 11/2013 | Dough et al. |
| 9,041,933 B2 | 5/2015 | Kharrat et al. |
| 9,278,351 B2 | 3/2016 | Mostowfi et al. |
| 9,346,049 B2 | 5/2016 | Mostowfi et al. |
| 10,379,100 B2 | 8/2019 | Mostowfi et al. |
| 11,035,839 B2 * | 6/2021 | Sieben .................... E21B 49/08 |
| 2011/0062058 A1 | 3/2011 | Rogel et al. |
| 2013/0067991 A1 | 3/2013 | Schabron et al. |
| 2013/0242288 A1 | 9/2013 | Kharrat et al. |
| 2015/0036136 A1 | 2/2015 | Kharrat et al. |
| 2018/0164273 A1 | 6/2018 | Sieben et al. |

FOREIGN PATENT DOCUMENTS

| | | |
|---|---|---|
| EP | 0245512 A1 | 11/1987 |
| EP | 0561789 A1 | 9/1993 |
| EP | 2609415 A1 | 7/2013 |
| JP | H0694697 A * | 4/1994 |
| JP | 2011088964 A | 5/2011 |
| WO | 2011151746 A1 | 12/2011 |
| WO | 2012025845 A1 | 3/2012 |
| WO | 2012120537 A2 | 9/2012 |
| WO | 2013126732 A1 | 8/2013 |
| WO | 2013130932 A1 | 9/2013 |
| WO | 2015023343 A1 | 2/2015 |

OTHER PUBLICATIONS

ASTM Standard D2007-11, "Test Method for Characteristic Groups in Rubber Extender and Processing Oils and Other Petroleum-Derived Oils by the Clay-Gel Absorption Chromatographic Method", 2011, 8 pages.
ASTM Standard D3279-12, "Test Method for n-Heptane Insolubles, ASTM International", 2001, 4 pages.
ASTM Standard D4124-09, "Test Method for Separation of Asphalt into Four Fractions", 2009, 8 pages.
ASTM Standard D6560-00, "Standard Test Method for Determination of Asphaltenes (Heptane Insolubles) in Crude Petroleum and Petroleum Products", 2000, 6 pages.
Boysen, R.B. et al., "The automated asphaltene determinator coupled with saturates, aromatics, and resins separation for petroleum residua characterization", Energy Fuels, 2013, 27(8), pp. 4654-4661.
Chaffin, J. M. et al., "The use of HPLC to determine the saturate content of heavy petroleum products", Journal of Liquid Chromatography and Related Technologies, 1996, 19(10), pp. 1669-1682.
Corbett, L.W., "Composition of asphalt based on generic fractionation, using solvent deasphaltening, elution-adsorption chromatography, and densimetric characterization", Analytical Chemistry, 1969, 41(4), pp. 576-579.
Fan, T. et al., "Rapid and Accurate SARA Analysis of Medium Gravity Crude Oils", Energy Fuels, 2002, 16(6), pp. 1571-1575.
Fan, T. et al., "Evaluating Crude Oils by SARA Analysis. In SPE/DOE Thirteenth Symposium on Improved Oil Recovery", 2002,. pp. 883-889.
Fuhr, B. J. et al., "Comparison of bitumen fractionation methods", Energy and Fuels, 2005, 19(4), pp. 1327-1329.
Grizzle, P. L. et al., "Automated liquid chromatographic compound class group-type separation of crude oils and bitumens using chemically bonded aminosilane", Analytical Chemistry, 1986, 58(12), pp. 2389-2396.
Jewell, D. M. et al., "Ion-exchange, coordination, and adsorption chromatographic separation of heavy-end petroleum distillates", Analytical Chemistry, 1972, 44(8), pp. 1391-1395.
Kharrat, A. M. et al., "Issues with Comparing SARA Methodologies", Energy Fuels, 2007, 21, pp. 3618-3621.
Melendez, L. V. et al., "Prediction of the SARA analysis of Colombian crude oils using ATR-FTIR spectroscopy and chemometric methods", Journal of Petroleum Science and Engineering, 2012, 90-91, pp. 56-60.
Miller, R., "Hydrocarbon class fractionation with bonded-phase liquid chromatography", Analytical Chemistry, 1982, 54(11), pp. 1742-1746.
Molina, V. D. et al., Correlations between SARA fractions and physicochemical properties with 1H NMR spectra of vacuum residues from Colombian crude oils. Fuel, 2010, 89(1), pp. 185-192.
Radke, M. et al., "Class separation of aromatic compounds in rock extracts and fossil fuels by liquid chromatography", Analytical Chemistry®, 1984, 56(13), pp. 2538-2546.
Ruiz-Morales, Y. et al., "Electronic Absorption Edge of Crude Oils and Asphaltenes Analyzed by Molecular Orbital Calculations with Optical Spectroscopy", Energy Fuels, 2007, 21(2), pp. 944-952.
Sanchez-Minero, F. et al., "Predicting SARA composition of crude oil by means of NMR", Fuel, 2013, 110, pp. 318-321.
Sinnathamb, C. M. et al., "Relationship Between SARA Fractions and Crude Oil Fouling", Journal of Applied Sciences, 2012, 12(23), pp. 2479-2483.
Suatoni, J. C. et al., "Rapid Hydrocarbon Group-Type Analysis by High Performance Liquid Chromatography", Journal of Chromatographic Science, 1975, 13(8), pp. 361-366.
Wiehe, I. A et al., "The Oil Compatibility Model and Crude Oil Incompatibility", Energy Fuels, 1999, 14(1), pp. 56-59.
Nguyen, N-T et al., "Micromixers—a Review", Journal of Micromechanics and Microgngineering, 2005, 15(2). 17 pages.
Schneider, M. H. et al., "Measurement of Asphaltenes Using Optical Spectroscopy on a Microfluidic Platform", Analytical Chemistry, 2013, 85(10), pp. 5153-5160.

(56) References Cited

OTHER PUBLICATIONS

Sieben et al., Optical Measurement of Saturates, Aromatics, Resins, and Alsphaltenes in Crude Oil, Energy Fuels, vol. 31, Mar. 31, 2017, pp. 3684-3697.
International Search Report and Written Opinion of International Patent Application No. PCT/US2015/034695 dated Mar. 28, 2016, 9 pages.
International Preliminary Report on Patentability of International Patent Application No. PCT/US2015/034695, dated Dec. 12, 2017, 5 pages.
Speight, J.G., 1999. The Chemistry and Technology of Petroleum 3rd ed., CRC Press, pp. 18 and 212.
Mullins, O.C., 2007. Asphaltenes, heavy oils, and petroleomics, Springer, p. 594.
Aske, 2002, Characterisation of Crude Oil Components, Asphaltene Aggregation and Emulsion Statbility by means of Near Infrared Spectroscopy and Multivariate Analysis, PHD Thesis, Jun. 2002 (58 pages).
Marioli, 2011, Application of nonaqueous capillary electrophoresis in alphaltene analysis, MSC Thesis, Jul. 29, 2011 (30 pages).
Moy et al., 2013, A Novel Petrochemsitry Solution: SARA Fractionation of Crude Oil Using an Adaptable Gilson MPLC System—Technical Note 0312, Jan. 11, 2013 (6 pages).
Ali Chamkalani, 2013, Assessment of asphaltene deposition due to titration technique, Fluid Phase Equilibria 339 (2013) pp. 72-80.

\* cited by examiner

AUTOMATED METHOD AND APPARATUS FOR MEASURING SATURATE, AROMATIC, RESIN, AND ASPHALTENE FRACTIONS USING MICROFLUIDICS AND SPECTROSCOPY

CROSS-REFERENCE TO RELATED APPLICATIONS

This application is a Divisional Application of U.S. application Ser. No. 15/579,271 filed Dec. 4, 2017, now U.S. Pat. No. 11,035,839, and is a National Stage Entry of PCT/US2015/034695, filed Jun. 8, 2015, the disclosure of which is incorporated herein by reference.

BACKGROUND

Field

The present application relates to methods and apparatus for measuring the fractions of saturates, aromatics, resins, and asphaltenes in a sample of crude oil.

Related Art

Petroleum composition data plays a role in guiding both upstream and downstream operations, including: predicting fluid behavior inside a petroleum reservoir, providing flow assurance during transportation of the petroleum, understanding potential outcomes when mixing or blending or diluting the petroleum, and directing refinement processes. Separating crude oil into its constituent parts or "fractions" is a fundamental operation when characterizing the composition of the crude oil. Once separated, the fractions can be quantified and analyzed. One of the most widely used compositional analyses for petroleum samples is SARA fractionation, which separates the oil into four parts based on molecular polarizability: saturates, aromatics, resins, and asphaltenes. The fractions are then gravimetrically weighed and reported as a mass percentage of the initial whole oil; for instance, an oil could be composed of 50% saturates, 25% aromatics, 15% resins and 10% asphaltenes, in weight percentages.

The saturate hydrocarbon fraction is non-polar and is composed of normal alkanes, branched alkanes, and cycloalkanes. The aromatic hydrocarbon fraction is polar and contains molecules that have alternating double and single bonds between carbon atoms producing conjugated electron orbital systems. The last two SARA fractions, resins and asphaltenes, are alkylated aromatic polycyclic clusters with incorporated alkyl side-chains, heteroatoms (N, S, O) and trace metals (e.g., Ni, V, Fe) and they are the most polar fractions of crude oil. The difference between these two fractions is in their solubility profile. Resins are defined as being soluble in n-alkanes like pentane or heptane. Conversely, asphaltenes are arbitrarily defined as being insoluble in light n-alkanes, but soluble in toluene or dichloromethane.

There are many variations of the SARA test and they are generally referred to as standard methods. However, seemingly small modifications to a SARA procedure, either by design or by human error, can produce notably different fractionation results. Historically this has led to inconsistent percentages reported to end users, who are not commonly aware of the analytical details employed. This is particularly true when data is generated from commercial laboratories that use modified standard procedures and proprietary methods. Furthermore, the SARA procedure often involves several days of qualified technician time making the technique expensive to perform.

BRIEF SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method and apparatus for determining the fractions of saturates, aromatics, resins, and asphaltenes of a hydrocarbon fluid sample. The method (and corresponding apparatus) involves a sequence of operations including:

i) performing a microfluidic mixing operation that forms a mixture that includes the hydrocarbon fluid sample and a solvent fluid that dissolves asphaltenes;
ii) performing optical spectroscopy on the hydrocarbon fluid sample-solvent fluid mixture resulting from i);
iii) performing a microfluidic mixing operation that forms a mixture that includes the hydrocarbon fluid sample and a titrant fluid that precipitates asphaltenes;
iv) using a microfluidic process that results in precipitation of asphaltenes from the hydrocarbon fluid sample-titrant fluid mixture resulting from iii);
v) performing a microfluidic filtering operation that removes precipitated asphaltenes from the mixture resulting from iv) while outputting permeate;
vi) performing optical spectroscopy on the permeate resulting from v);
vii) determining an asphaltene fraction percentage of the hydrocarbon fluid sample based on the optical spectroscopy performed in ii) and vi);
viii) sequentially separating a saturate-containing portion, an aromatic-containing portion, and a resin-containing portion from the permeate from v);
ix) for each separating of viii), measuring an optical property of the respective saturate-, aromatic-, and resin-containing portions over time; and
x) determining fraction percentages of saturates, aromatics, and resins in the hydrocarbon fluid sample based on the measured optical properties of ix) and respective mass-to-optical correlation data for saturates, aromatics, and resins.

In one embodiment, the microfluidic mixing operations of i) and iii), the microfluidic process of iv), and the microfluidic filtering operation of v) are performed by at least one microfluidic chip. The at least one microfluidic chip may include first and second inlet ports that are fluidly coupled to a mixer section. The first inlet port may be configured to supply the solvent fluid and the titrant fluid to the mixer section for use in conjunction with the microfluidic mixing operations of i) and iii). The second inlet port may be configured to supply the hydrocarbon fluid sample to the mixer section for use in conjunction with the microfluidic mixing operations of i) and iii).

In one embodiment, the at least one microfluidic chip comprises a reactor section fluidly coupled downstream from the mixer section. The at least one microfluidic chip may comprise a membrane filter section fluidly coupled downstream from the reactor section. The membrane filter section may lead to both a waste port and an outlet port.

In one embodiment the microfluidic mixing operations of i) and iii) and the microfluidic process of iv) are performed by a first microfluidic chip and the microfluidic filtering operation of v) is performed by a second microfluidic chip that is separate and distinct from the first microfluidic chip and fluidly coupled to the first microfluidic chip.

In one embodiment, the optical spectroscopy of ii) and vi) involves the hydrocarbon fluid sample-solvent fluid mixture resulting from i) and the permeate resulting from v) passing through a flowthrough optical cell, where the flowthrough optical cell is optically coupled to a corresponding spectrometer.

In one embodiment, the operations of i) to x) are part of an automated workflow involving automatic control of the flow rate of the hydrocarbon fluid sample and the solvent fluid that are mixed in i), and the hydrocarbon fluid sample and the titrant fluid that are mixed in iii) as well as automatic control of the optical spectroscopy of ii) and vi).

The optical property measured for the saturate-containing portion can be refractive index and the optical property measured for the aromatic-containing portion and the resin-containing portion can be absorbance from the ultraviolet to the infrared range.

Determining the fraction percentages of saturates, aromatics, and resins in the hydrocarbon fluid sample can include calculating mass fractions of saturates, aromatics, and resins based on predetermined linear correlations obtained empirically between the optical property and mass for saturates, aromatics, and resins.

The hydrocarbon fluid sample can be selected from the group consisting of a crude oil sample, a blend of different crude oils, and one or more additives combined with crude oil. The solvent fluid used for the method can be selected from the group consisting of toluene, dichloromethane (DCM), xylenes, benzene, methyl naphthalene, cyclohexane, tetrahydrofuran (THF), chloroform, trichloroethylene, tetrachloroethylene, and carbon tetrachloride. The titrant fluid used for the method can be selected from the group consisting of n-heptane, n-hexane, n-pentane, petroleum ether, ethyl acetate, and alcohols.

DETAILED DESCRIPTION

Figure 1:
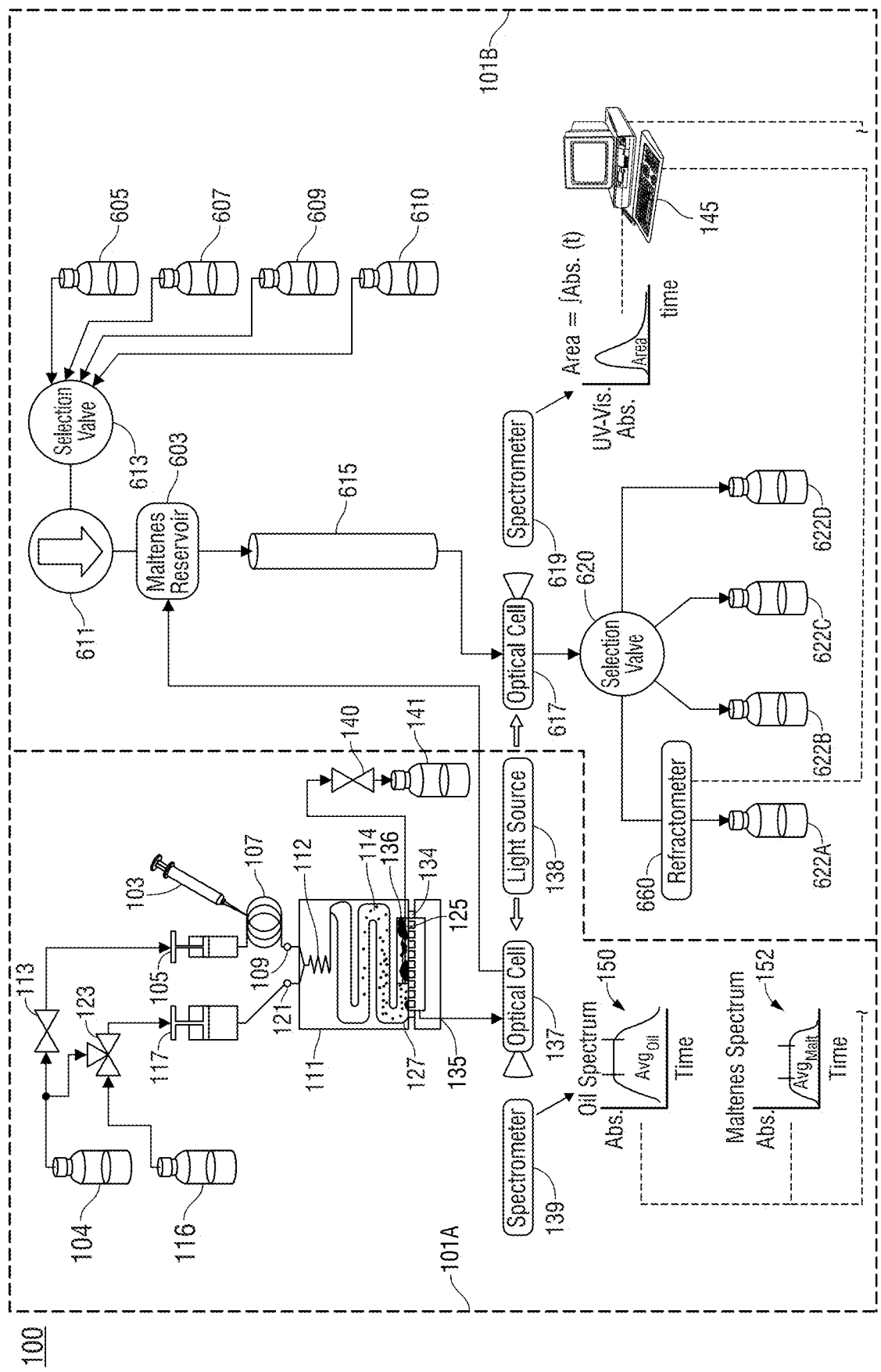
FIG. 1 is a schematic diagram of an automated test apparatus configured to analyze the asphaltene, saturate, aromatic, and resin fractions of a hydrocarbon fluid sample in accordance with the present disclosure.

Illustrative embodiments of the disclosed subject matter of the application are described below. In the interest of clarity, not all features of an actual implementation are described in this specification. It will of course be appreciated that in the development of any such actual embodiment, numerous implementation-specific decisions can be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As used herein, the term "microfluidics" or "microfluidic" refers to a device, apparatus, or system that deals with the behavior, precise control, and manipulation of fluids that are geometrically constrained to a small, commonly sub-millimeter, scale. The device, apparatus, or system can employ small, commonly sub-millimeter, scale channels that are etched into planar substrates, such as glass, where networks of these embedded channels transport the sample from one operation to the next. The manipulation of small volumes of fluid enables precise control of reagents and seamless automation of several consecutive operations.

The subject matter of the disclosure relates generally to characterizing crude oil fractions. There are two main approaches to perform a SARA test: 1) utilizing conventional glassware and large column liquid chromatography followed by gravimetric measurements, and 2) employing other faster and smaller-scale separation techniques followed by non-gravimetric measurement of the fractions. Jewel et al. and Corbett pioneered the conventional approach nearly half a century ago, which led to the creation of standard methods like ASTM D2007 (ASTM Standard D2007-11 2011) and ASTM D4124 (ASTM Standard D4124-09 2009). Initially, the asphaltene content of the crude oil sample is measured through a procedure similar to those mentioned in standard methods like ASTM D3279 (ASTM Standard D3279-12 2001) or ASTM D6560 (ASTM Standard D6560-00 2000). The remaining fractions are saturates, aromatics, and resins (SAR), collectively referred to as petrolenes, maltenes, or deasphalted oil. The maltenes are separated using normal-phase liquid chromatography based on stationary phases comprised of clay, alumina, silica, and/or combinations thereof. The maltenes are injected onto the stationary phase and separation of the various fractions is accomplished by sequentially increasing the eluents polarity and capturing the eluates. The collected fractions are then concentrated by vacuum evaporation of the elution solvent to recover the mass of the solute. As a quality check, the masses of the three fractions are summed and compared to the injected maltenes mass to determine the percent recovery—otherwise known as mass balance. This conventional gravimetric method is time consuming, is difficult to automate, consumes large volumes of solvents, and is intractably variable from one laboratory to the next.

The second approach to SARA testing aims to address the issues noted with the manual SARA techniques by providing answers more rapidly and by increasing automation/standardization to remove operator bias and improve laboratory-to-laboratory consistency. Various strategies have been explored ranging from: high performance liquid chromatography (HPLC) (Suatoni, J. C. & Swab, R. E., "Rapid hydrocarbon group type analysis by high performance liquid chromatography," *Journal of Chromatographic Science*, 13(8), 1975, pp. 361-366), bonded stationary phases and refractive index measurement for saturates (Miller, R., "Hydrocarbon class fractionation with bonded-phase liquid chromatography. *Analytical Chemistry*, 54(11), 1982, pp. 1742-1746), moisture-controlled HPLC (Radke, M., Willsch, H., & Welte, D. H., "Class separation of aromatic compounds in rock extracts and fossil fuels by liquid chromatography," *Analytical Chemistry*, 56(13), 1984, pp. 2538-2546), automated HPLC (Grizzle, P. L. & Sablotny, D. M., "Automated liquid chromatographic compound class group-type separation of crude oils and bitumens using chemically bonded aminosilane," *Analytical Chemistry*, 58(12), 1986, pp. 2389-2396; and Chaffin, J. M. et al., "The use of HPLC to determine the saturate content of heavy petroleum products," *Journal of Liquid Chromatography and Related Technologies*, 19(10), 1996, pp. 1669-1682), thin layer chromatography equipped with a flame ionization detector (Fan, T. & Buckley, J. S., "Rapid and Accurate SARA Analysis of Medium Gravity Crude Oils," *Energy & Fuels*, 16(6), 2002, pp. 1571-1575; and Fuhr, B. J. et al., "Comparison of bitumen fractionation methods," *Energy & Fuels*, 19(4), 2005, pp. 1327-1329), infrared spectroscopy and principal component analysis (Meléndez, L. V. et al., "Prediction of the SARA analysis of Colombian crude oils using ATR-FTIR spectroscopy and chemometric methods," *Journal of Petroleum Science and Engineering*, 90-91, 2012, pp. 56-60; and Aske, N., Kallevik, H. & Sjöblom, J., "Determination of saturate, aromatic, resin, and asphaltenic (SARA) components in crude oils by means of infrared and near-infrared spectroscopy," *Energy & Fuels*, 15(5), 2001, pp. 1304-1312), automated multi-column system with UV-Vis and evaporative light scattering detectors (Boysen, R. B. & Schabron, J. F., "The automated asphaltene determinator coupled with saturates, aromatics, and resins separation for petroleum residua characterization," *Energy & Fuels*, 27(8), 2013, pp. 4654-4661) and NMR (Sanchez-Minero, F. et al., "Predicting SARA composition of crude oil by means of NMR," *Fuel*, 110, 2013, pp. 318-321; and Molina V, D., Uribe, U. N. & Murgich, J., "Correlations between SARA fractions and physicochemical properties with 1H NMR spectra of vacuum residues from Colombian crude oils," *Fuel*, 89(1), 2010, pp. 185-192). These strategies rely on alternative detection systems to replace gravimetric measurement. However, the studies often have limited sample sets that correlate new sensing approaches to the conventional gravimetric results. A large data set that includes diverse samples (light to heavy oils) is required to ensure robust predictive capabilities. Direct comparisons with ASTM D3279 and ASTM D6560 become challenging as many of the HPLC protocols for fractionation deviate substantially from the standard methods.

It is well known that saturates are transparent in the visible spectrum (Vis), but can be detected by using refractive index (RI). A correlation or response factor (RF) to mass is similar regardless of crude oil source, where the refractive index approaches a limiting value as chain length increases (Chaffin, J. M. et al., "The use of HPLC to determine the saturate content of heavy petroleum products," *Journal of Liquid Chromatography and Related Technologies*, 19(10), 1996, pp. 1669-1682). Aromatic compounds absorb strongly in the ultraviolet (UV) spectrum and as ring number and complexity increases, they absorb partially in the visible spectrum possessing a yellow to orange color. The resin and asphaltene fractions absorb broadly in the UV and visible wavelengths with coloration beyond 600 nm (Ruiz-Morales, Y., Wu, X. & Mullins, O. C., "Electronic Absorption Edge of Crude Oils and Asphaltenes Analyzed by Molecular Orbital Calculations with Optical Spectroscopy," *Energy & Fuels*, 21(2), 2007, pp. 944-952). The wide absorption in the resin and asphaltene fractions yields the brown to black coloration characteristic of crude oil. When all SARA fractions are combined, the coloration that results is the superposition of the spectra from each fraction, derived from the fraction's molecular species distribution. Generally, the UV-Vis absorption spectrum is fairly similar from oil-to-oil and is exponentially decaying from ultraviolet toward visible wavelengths. The characteristic decay can be described as an Urbach edge (Ruiz-Morales, Y., Wu, X. & Mullins, O. C., "Electronic Absorption Edge of Crude Oils and Asphaltenes Analyzed by Molecular Orbital Calculations with Optical Spectroscopy," *Energy & Fuels*, 21(2), 2007, pp. 944-952).

This disclosure presents a rapid and automated method for rapidly separating and measuring four sub-fractions of crude oil: saturates, aromatics, resins, and asphaltenes (SARA).

FIG. 1 depicts an illustrative embodiment of an apparatus 100 for automated fluid analysis of a crude oil sample. The apparatus 100 includes a first portion 101A that characterizes the asphaltene fraction using microfluidics and spectroscopy and a second portion 101B that characterizes the maltenes using chromatography and spectroscopy. A first workflow is performed using the first portion 101A that produces a stream of permeate which includes maltenes. The permeate is introduced into the second portion 101B, which is used to perform a second workflow to characterize the maltenes in the permeate.

The first portion 101A includes a reservoir 103 (shown as a syringe) that holds a crude oil sample and sample loop 107 with a defined volume. The crude oil sample can include lighter (more volatile) molecular weight crude oil components as well as heavy (less volatile) molecular weight components such as heavy oil and bitumen. The syringe 103 can be operated to inject a defined volumetric plug of the crude oil sample held by the syringe 103 into the defined volume of the sample loop 107. Auto-samplers may also be incorporated to further automate the apparatus. The apparatus 100 also includes a reservoir 104 fluidly coupled to an electrically-controlled pump 105 by a valve 113. The reservoir 104 holds a fluid (referred to herein aa a "solvent") that dissolves asphaltene solids when present in a crude oil sample. The solvent can be toluene, dichloromethane (DCM), xylenes, benzene, methyl naphthalene, cyclohexane, tetrahydrofuran (THF), chloroform, trichloroethylene, tetrachloroethylene, carbon tetrachloride, carbon disulfide, and other suitable solvents. The reservoir 104 and the pump 105 are operated to motivate (or push) the defined volumetric plug of the crude oil sample loaded into the sample loop 107 from syringe 103 such that it flows (for example, at or near a desired flow rate) into an inlet port 109 of microfluidic chip 111. The pump 105 can be an electrically-controlled syringe pump, such as the Mitos Duo XS-Pump available from The Dolomite Center Limited of Royston, UK, where the syringe of the pump acts as the reservoir 104 that stores the solvent. Also, the pump 105 can be operated to introduce solvent from reservoir 104 alone, without a crude oil sample.

The first portion 101A also includes a reservoir 116 and an electrically-controlled pump 117 that is fluidly coupled to the reservoir 116, and to the reservoir 104, by a valve 123. The reservoir 116 holds a fluid (referred to herein as a "precipitant") that causes asphaltenes to precipitate from a crude oil sample when present. The precipitant can be an n-alkane (such as n-heptane ($C_7H_{16}$), n-hexane ($C_6H_{14}$), or n-pentane ($C_5H_{12}$)) or other solvents, such as petroleum ether, ethyl acetate, alcohols or any other solvent which can cause asphaltene precipitation due to a limited solubility. The precipitant from pump 117 flows (for example, at or near a desired flow rate) into an inlet port 121 of the microfluidic chip 111. The pump 117 can also be used to pump solvent from reservoir 104 directly into microfluidic chip 111 without the solvent passing through sample loop 107.

In one embodiment, flow of fluid from pump 117 and pump 105 can be combined in a mixing section 112 of the microfluidic chip 111. The mixing section 112 includes a y-type junction that leads from the two inlet ports 109, 121 to a section that provides microfluidic mixing of the fluids introduced into the inlet ports 109, 121. The mixing section 112 can employ chaotic split and recombine microfluidic mixing techniques or other suitable microfluidic techniques as described in Nguyen, N-T and Wu, Z., "Micromixers—a Review," *Journal of Micromechanics and Microengineering* 15, No. 2 (2005): R1, herein incorporated by reference in its entirety.

The pumps 117, 105 can be operated to inject the precipitant alone, the solvent alone, or a mixture of a controlled ratio of the precipitant and the solvent into the mixing section 112 of the microfluidic chip 111. The pumps 117, 105 can be electrically-controlled syringe pumps, such as the Mitos Duo XS-Pump, where the syringe of the respective syringe pumps acts as the reservoirs 116, 104 that hold an amount of the precipitant and the solvent, respectively.

As noted above, the microfluidic chip 111 includes mixing section 112 that provides microfluidic mixing of the fluids introduced into inlet ports 121 and 109. The microfluidic chip 111 also includes a reactor section 114 that provides a microfluidic flowpath that allows for microfluidic processes where solid asphaltene content (commonly referred to as asphaltene floccules or asphaltene flocks) precipitate from the mixture generated by the mixing section 112. The reactor section 114 is realized by a serpentine path that has larger cross-sectional area as compared to the channel(s) of the mixing section 112. The reactor section 114 also includes an outlet port 125 at the downstream end of the reactor section 114 flowpath. The asphaltene flock is carried as a suspension in the liquid phase content of the mixture. The liquid phase content of the mixture includes maltenes of the crude oil sample, which are the lower molecular weight components of the crude oil sample that remain after removing the precipitated asphaltene content. The maltenes are also soluble in the precipitant. Note that the smaller dimensions of the mixing section 112 enable more effective and rapid mixing because of shorter diffusion distances and the larger dimensions of the reactor section 114 allow asphaltene floccules to grow to a larger size for retainment by the filter section 134 as described below.

The outlet port 125 is fluidly coupled to a filter section 134 that includes a membrane filter providing microfluidic filtering that is configured to trap solid phase hydrocarbon components (i.e., the asphaltene flock) while passing soluble liquid phase hydrocarbon components (the permeate, which includes the maltenes of the crude oil sample) to an outlet port 135 of the microfluidic chip 111. The filter section 134 of the microfluidic chip 111 can also be fluidly coupled to a waste port 136 that allows for flushing and removal of the solid phase hydrocarbon components (i.e., the asphaltene flock) that is trapped by the filter section 134 of the microfluidic chip 111.

In one embodiment, the filter section 134 and the outlet port 135 are formed on a second microfluidic chip that is separate and distinct from the microfluidic chip 111 but is fluidly coupled to microfluidic chip 111.

The outlet port 135 of the microfluidic chip 111 is fluidly coupled to the inlet of a flowthrough optical cell 137. A spectrometer 139 is optically coupled to flowthrough optical cell 137 and can be operated to derive an optical spectrum of the fluid that flows from the outlet 135 through flowthrough optical cell 137.

In one embodiment, flowthrough optical cell 137 can be realized by an optical absorbance flow cell, such as the FIAlab SMA-Z-2.5 cell with fused silica windows and a 2.5 mm optical path and and a 2.0 microliter internal volume available from FIAlab Instruments, Inc. of Bellevue, Washington, USA. Custom flow cells that are either machined in the microfluidic chip holders or integrated directly on the microfluidic chip can also be used. The spectrometer 139 can be realized by a broadband spectrometer, such as the model HR2000+ available from Ocean Optics, Inc. of Dunedin, Florida, USA. The broadband spectrometer can be used in conjunction with a broadband light source 138 which can be based on a tungsten filament bulb (such as the model LS-1 light source available from Ocean Optics, Inc.). Fiber optic waveguides can be used to optically couple the optical cell 137 to both the broadband light source 138 and spectrometer 139.

Optical cell 137 is fluidly coupled to a maltenes sample reservoir 603. The maltenes sample reservoir 603 is coupled to a pump 611, which is coupled to a selection valve 613. The selection valve 613 can be selectively fluidly coupled to any one of a first solvent reservoir 605, a second solvent reservoir 607, a third solvent reservoir 609, and a fourth solvent reservoir 610. It should be noted that valve 613 may be replaced by as many as four independent valves and multiple independent pumps may be used in place of pump 611, in which case valve or valves 613 may be omitted. Maltenes sample reservoir 603 is in fluid communication with a packed bed 615, as is pump 611, and the packed bed 615 is in further fluid communication with a flowthrough optical cell 617. Optical cell 617 is operably associated with light source 138 and optically coupled to a spectrometer 619, which is also operably associated with a computer system 145.

The first solvent reservoir 605 is configured to store a solvent that is suitable to elute saturates from the permeate, for example n-heptane or the like. The second solvent reservoir 607 is configured to store a solvent that is suitable to elute aromatics from the permeate, for example toluene or the like. The third solvent reservoir 609 is configured to store a solvent that is suitable to elute resins from the permeate, for example a mixture of trichloromethane and isopropyl alcohol, which may be a mixture comprising about 98 percent by volume trichloromethane and about 2 percent by volume isopropyl alcohol, or the like. The fourth solvent reservoir 610 is configured to store a solvent that is suitable to elute resins from the permeate, for example a mixture of trichloromethane and isopropyl alcohol, which may be a mixture comprising about 50 percent by volume trichloromethane and about 50 percent by volume isopropyl alcohol, or the like.

Pump 611 is configured to selectively urge a solvent from one of solvent reservoirs 605, 607, 609, and 610 depending upon the state of valve 613. Pump 611 selectively urges solvent through the maltenes reservoir 603 into packed bed 615.

In one illustrative embodiment, the packed bed 615 can be a column of packed alumina or silica, for example, exhibiting a grain size within a range of about 80 mesh to about 200 mesh, having an inlet in fluid communication with pump 611 and an outlet in fluid communication with flowthrough optical cell 617. In one embodiment, flowthrough optical cell 617 can incorporate a cuvette, such as a cuvette having a light path of about five millimeters and a volume of about 195 microliters, such as is available from Starna Cells, Inc. of Atascadero, California, USA. In one embodiment, the flowthrough optical cell 617 can be realized by an optical absorbance flow cell, such as the FIAlab SMA-Z-2.5 cell with fused silica windows and a 2.5 mm optical path and a 2.0 microliter internal volume. The spectrometer 619 can be realized by a broadband spectrometer, such as the model HR2000+ with an associated model DT-mini 2B light source, available from Ocean Optics, Inc. Fiber optic waveguides can be used to optically couple the flowthrough optical cell 617 to both the light source 138 and the spectrometer 619.

Computer system 145 may be, in various embodiments, any suitable computer configured to process data generated by spectrometer 619, such as a microcomputer or the like. In one embodiment, computer system 145 operates analysis software, for example Spectra Suite software available from Ocean Optics, Inc.

For the case where the packed bed 615 is a column of packed alumina, the packed bed 615 can be prepared by activating alumina in a furnace having a temperature of about 430° C. for a period of about 24 hours. The alumina can then be cooled to ambient temperature in a desiccator and introduced into the column and wetted using n-heptane, or the like. In another embodiment, the packed bed 615 can be a column of packed stationary phase silica gel. The gel can be regenerated by heat treatment at 130° C. for about one hour before use.

A selection valve 620 is fluidly coupled to an outlet of the optical cell 617 to selectively direct fluid from the packed bed 615 into one of a plurality of collection reservoirs 622A-622D. Also, a refractometer 660 is fluidly coupled between the selection valve 620 and saturate collection reservoir 622A.

Computer system 145 can be programmed with suitable control logic that interfaces to the electrically-controlled pumps 105, 117 via wired or wireless signal paths therebetween, and that interfaces to the electrically-controlled valves 113, 123, 613, 620 via wired or wireless signal paths therebetween. The computer system 145 can also interface to the spectrometers 139, 619 and the refractometer 660 via wired or wireless signal paths therebetween. The control logic of the computer system 145 (which can be embodied in software that is loaded from persistent memory and executed in the computing platform of the computer system 145) is configured to control the different parts of the apparatus 100 to carry out an automated sequence of operations (workflow) that characterizes the SARA fractions of an oil sample. The control logic can be configured by a testing script, which is input into and executed by the computer system 145 to perform automatic control operations as specified by the testing script. The computer system 145 can include a graphical user interface that allows the user to specify the sequence of automatic control operations and/or the parameters (such as pressures, flow rates, temperatures, etc.) for such automatic control operations. An example of such an automated workflow is shown in FIGS. 2 and 3.

Figure 2:
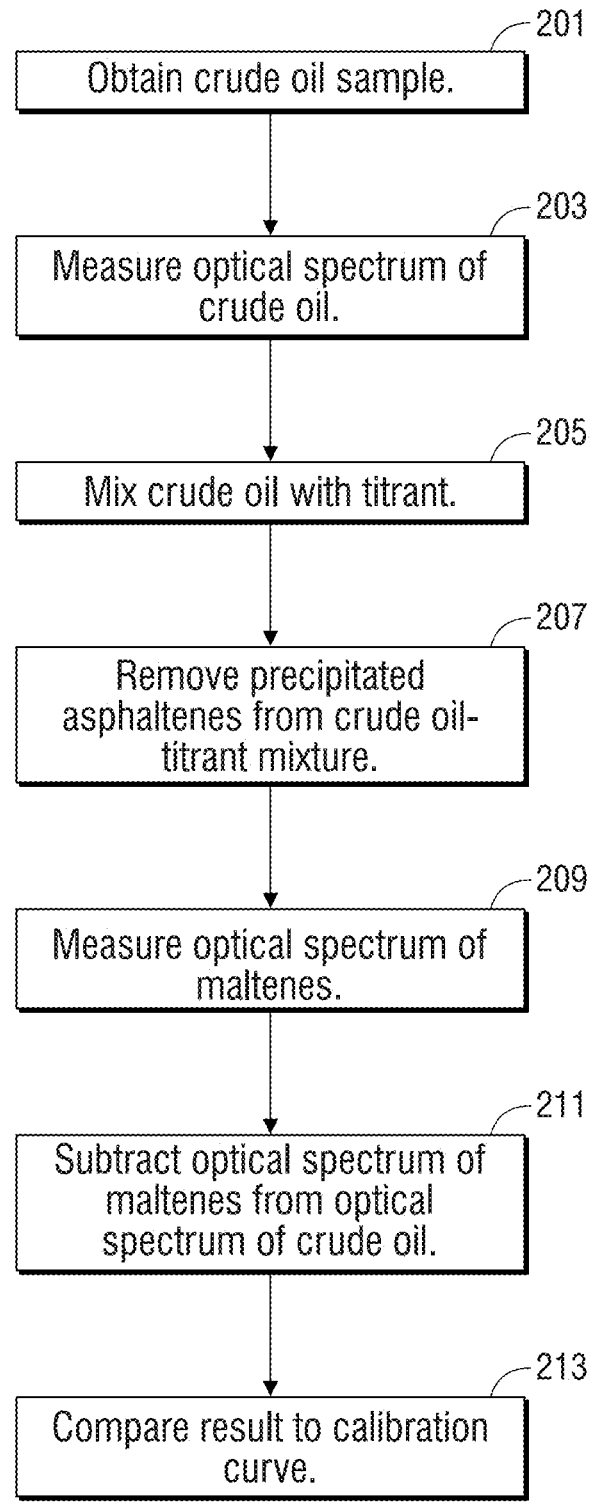
FIG. 2 is a workflow for determining the asphaltene fraction of the hydrocarbon sample in accordance with the present disclosure using the test apparatus of FIG. 1.
Figure 3:
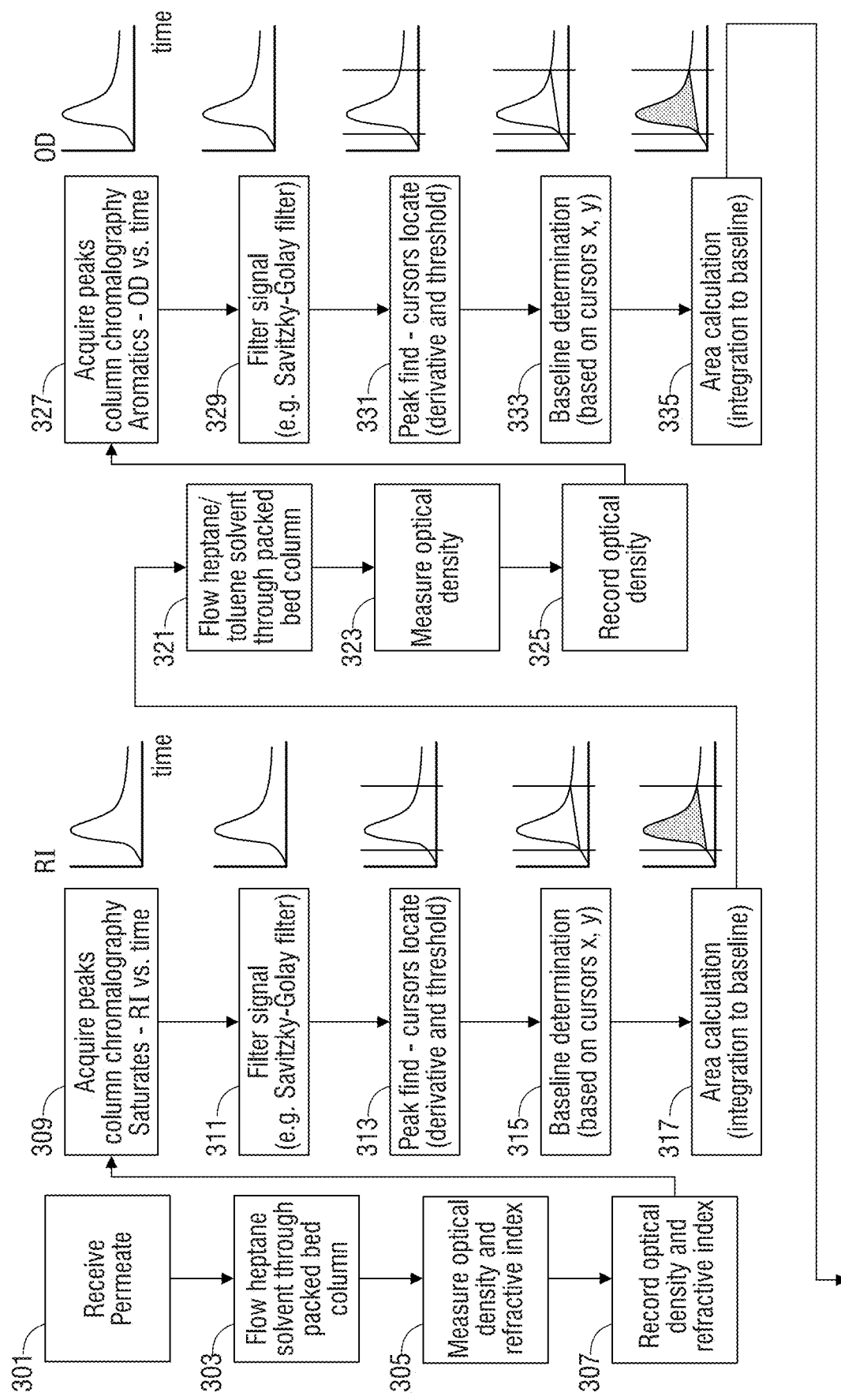
FIG. 3 is a workflow for determining the saturate, aromatic, and resin fractions of the hydrocarbon sample in accordance with the present disclosure using the test apparatus of FIG. 1.
Figure 3:
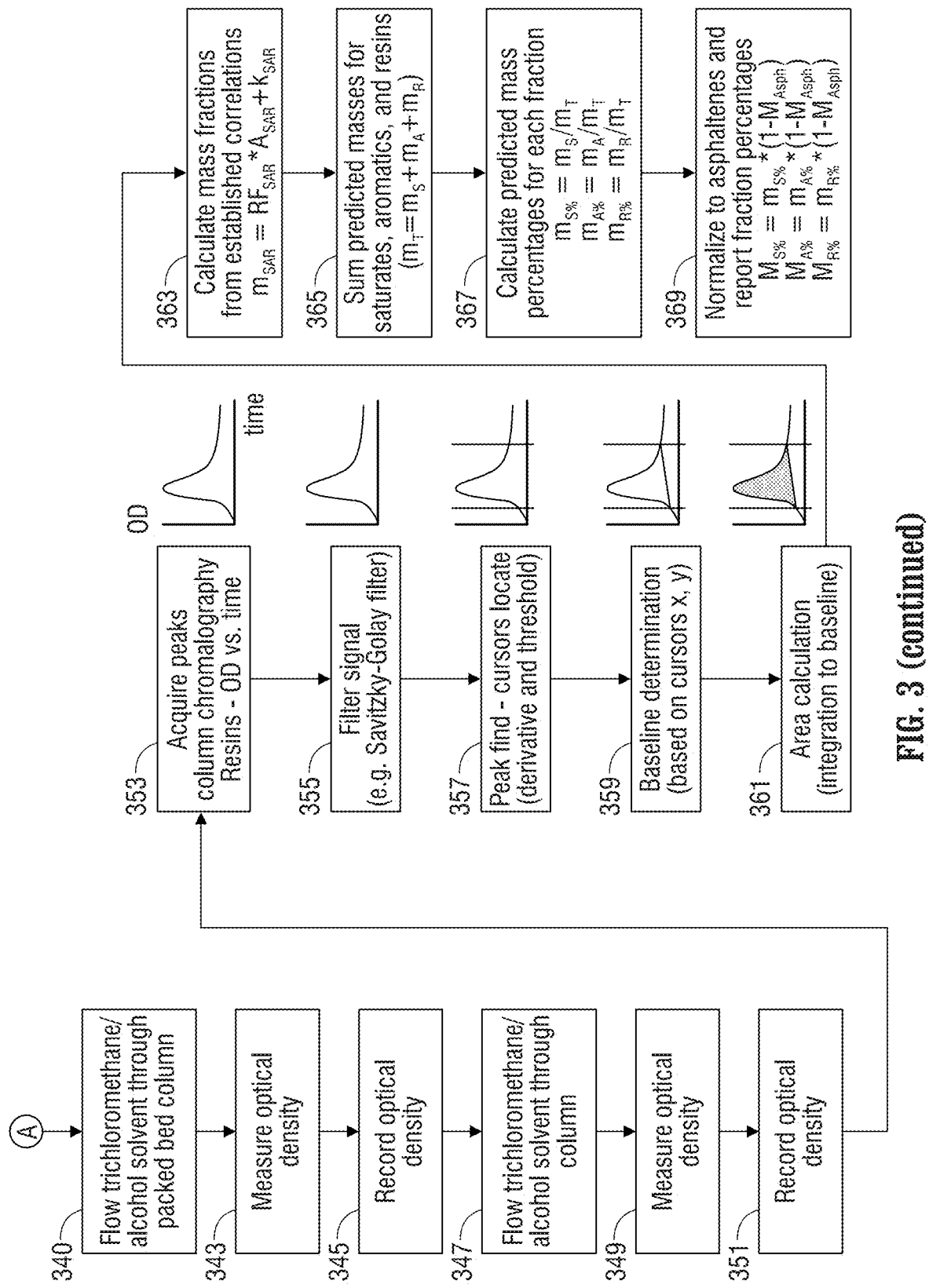

The workflow shown in FIG. 2 can be performed to measure the weight concentration of asphaltenes in a sample of crude oil and separate maltenes from a sample of crude oil from the asphaltenes for further analysis of the maltenes in the workflow shown in FIG. 3.

At 201, a sample of crude oil and a solvent (i.e., a toluene) are introduced to the mixing section 112 via inlet ports 109 and 121, respectively, by syringe 103, and by pump 117, respectively. The sample of crude oil and the solvent are mixed in the mixing section 112 at a predetermined ratio, such as at a ratio of about one part crude oil to about 80 parts solvent. The solvent aids in moving the crude oil through the microfluidic chip 111. The crude oil-solvent mixture is then passed through reactor section 114 of microfluidic chip 111 and filter section 134 of microfluidic chip 111 and to optical cell 137. The reactor section 114 of microfluidic chip 111 can allow the solvent of the sample/solvent mixture produced by the mixing section 112 to dissolve most if not all of the asphaltene content of the sample/solvent mixture (if any asphaltene content is present from the crude oil sample).

At 203 the spectrometer 139 analyzes the crude oil in optical cell 137 and determines an optical spectrum of the crude oil, represented by graph 150. In the illustrated embodiment, the optical spectrum of the crude oil, i.e., represented by graph 150, is fed to computer system 145. The computer system 145 is configured to store the optical spectrum 150 as measured in 203. The computer system 145 can determine the average oil absorbance ($Avg_{oil}$) from the optical spectrum data. Alternatively, the spectrometer 139 can be configured to analyze the crude oil sample and determine the average oil absorbance, which can then be stored in the computer system 145. The flow path of crude oil in first portion 101A is then cleaned.

It is not expected that asphaltenes will be collected by filter section 134 of microfluidic chip 111 during the operation of 203. However, in the event that asphaltenes are collected by the filter section 134 of microfluidic chip 111 during the operation of 203, a cleaning procedure can be executed to remove the collected asphaltenes before continuing to 205. This cleaning procedure can involve flowing solvent first across the membrane to the waste port 136 and second a solvent flush of the system.

At 205 valve 113 is initially closed. Next, a sample of crude oil is introduced into sample loop 107 via syringe 103. Thereafter valve 113 is opened and pump 105 is used to force the crude oil sample into mixing section 112 via inlet port 109. Simultaneously, valve 123 is opened from reservoir 116 to pump 117, and heptane (i.e., a titrant) is transmitted to inlet port 121 and mixing section 112 by pump 117. The flow rates for pumps 117 and 105 are configured such that mixing section 112 of microfluidic chip 111 forms a mixture where the crude oil sample is diluted with a predetermined concentration of the titrant. The sample of crude oil and the titrant are mixed in the mixing section 112 at a predetermined ratio, such as at a ratio of about one part crude oil to about 40 parts titrant.

At 207, once the sample of crude oil and the titrant are mixed, the titrant causes the asphaltenes in the crude oil to react in reactor section 114 and precipitate out in channel 127. Reactor section 114 of microfluidic chip 111 can allow the titrant of the sample/titrant mixture produced by mixing section 112 to precipitate out most if not all of the asphaltene content of the sample/titrant mixture (if any asphaltene content is present from the crude oil sample). The resultant sample/titrant mixture (including the precipitated solid-form asphaltene content) that is produced by reactor section 114 of microfluidic chip 111 flows downstream to outlet port 125 and then to filter section 134 of microfluidic chip 111, which traps the precipitated solid-form asphaltene content and allows the permeate (i.e., the liquid phase of the sample/titrant mixture) to pass to outlet port 135. The permeate flows from outlet port 135 and through the flowthrough optical cell 137 to maltenes reservoir 603.

In 209, spectrometer 139 is configured to measure an optical spectrum (represented by graph 152) of the permeate (which includes the maltenes of the crude oil sample) that flows through the corresponding flowthrough optical cell 137. In this manner, the spectrometer 139 measures an optical spectrum of the maltenes that flow from the microfluidic chip 111. Computer system 145 is further configured to store the optical spectrum of the maltenes as measured in 209.

At 209 computer system 145 can determine an average maltenes absorbance ($Avg_{Malt}$) from the optical spectrum data. Alternatively, spectrometer 139 can be configured to analyze the maltenes and determine the average maltenes absorbance, which can then be stored in computer system 145.

At 211 computer system 145 calculates an average asphaltene absorbance (optical density, $OD_{Asph}$) based on the average oil absorbance and the average maltenes absorbance as follows:

$$OD_{Asph} = 81/41 * Avg_{oil} - Avg_{Malt} \quad (1)$$

At 213, the asphaltene mass concentration ($M_{Asph}$) is determined based on predetermined calibration data (i.e., a linear correlation generating a response factor $RF_{Asph}$) and the optical density ($OD_{Asph}$) from the following relationship:

$$M_{Asph}(\%) = RF_{Asph} * OD_{Asph} \quad (2)$$

The calibration data correlates the optical spectrum of the asphaltene molecules to the asphaltene content measured using another technique, such as a conventional gravimetric technique, in which a series of crude oil samples are collected and tested, as described in U.S. Pat. No. 8,269,961, which is incorporated herein by reference.

It is expected that asphaltenes will be collected by the filter section 134 of microfluidic chip 111 during the operation of 209. In this case, a cleaning procedure can be executed to remove the collected asphaltenes before continuing to the operations of 211 and 213. Such a cleaning procedure can involve flowing solvent through microfluidic chip 111, waste port 136, and valve 140 to waste reservoir 141.

As noted above, graph 150 is a graphical representation of an illustrative optical spectrum of a crude oil, and graph 152 is a graphical representation of an illustrative optical spectrum of maltenes. The difference between these optical spectra is due to the optical spectrum of the asphaltenes in the crude oil. Note that the optical density or absorbance of the optical spectrum is at a relative maximum (or darkest in color) for the case of graph 150 since most of the asphaltene content of the crude oil sample is soluble and dissolved by the solvent, with very little precipitation of asphaltene content as well as very little filtration being performed by the microfluidic chip 111. The optical density or absorbance of the optical spectrum is at a relative minimum (or lightest in color) for the case of graph 152 since most of the asphaltene content of the crude oil sample is precipitated and removed by the filtration performed by the microfluidic chip 111 leaving an elution of maltenes and heptane solvent.

In 211, the computer system 145 processes the optical spectra measured and stored in 203 (with the asphaltene content present and dissolved in the crude oil sample/solvent mixture) in conjunction with the optical spectrum measured and stored in 209 (with the asphaltene content precipitated and removed from the crude oil sample/titrant mixture) in order to derive the weight fraction of asphaltene in the crude oil sample in 213. In one example, the processing of 211 can involve deriving a characteristic optical density or absorbance (AU) of the asphaltene content of the crude oil sample by the following equation:

$$AU = (OD@600 \text{ nm}_{Spectrum\ of\ 203} - OD@800 \text{ nm}_{Spectrum\ of\ 203}) - (OD@600 \text{ nm}_{Spectrum\ of\ 209} - OD@800 \text{ nm}_{Spectrum\ of\ 209}). \quad (3)$$

The first term of Eq. (3) is derived from the optical spectrum of 203 and represents the contribution of both asphaltene content and the maltenes to AU. The second term of Eq. (3) is derived from the optical spectrum of 209 and represents the contribution of the maltenes alone to AU. The subtraction of the optical density (OD) at 800 nm in both the first and second terms is meant to reduce the error from spectral offset introduced by light scattering and from other errors in the measurements. The characteristic optical density AU of the asphaltene content as derived from Eq. (3) can be correlated to a weight ratio of asphaltene content in the crude oil sample based upon calibration data. Such calibration data can define the relationship of the characteristic optical density AU of the asphaltene content to asphaltene content measurements in crude oil samples measured using some other technique (such as a conventional gravimetric technique, in which a series of crude oil samples are collected and tested). A correlation factor can be applied to convert the characteristic optical density AU of the asphaltene content to a weight ratio of asphaltene content in the crude oil sample as described in Schneider, M. H., Sieben, V. J., Kharrat, A. M., and Mostowfi, F., "Measurement of Asphaltenes Using Optical Spectroscopy on a Microfluidic Platform," *Analytical Chemistry* 85, No. 10 (2013): 5153-60, doi:10.1021/ac400495x, herein incorporated by reference in its entirety.

A workflow using the second portion 101B of apparatus 100 to measure the fractions of saturates, aromatics, and resins of a crude oil sample will now be described with reference to FIGS. 1 and 3.

At 301 the eluted maltenes and heptane solvent (i.e., the permeate) from the first portion 101A of apparatus 100 are received in maltenes reservoir 603 and flow into packed bed column 615. It is notable that the heptane solvent is present with the maltenes and is not removed (evaporated) from the maltenes prior to being introduced into packed bed 615, as is discussed in International Patent Application Publication No. WO 2012/025845. By not removing the heptane solvent, additional time can be saved in performing the SARA characterization analysis.

At 303 valve 613 is switched to place first solvent reservoir 605 in fluid communication with pump 611 and valve 620 is switched to place reservoir 622A into fluid communication with optical cell 617. Then, saturates fractionation begins at 303 by flowing n-heptane from first solvent reservoir 605 through pump 611 into packed bed column 615 at 2.5 ml/minute to elute the saturates of the maltenes portion in the packed bed 615. The non-polar saturate molecules have little to no interaction with the packed bed 615 and elute out, while the aromatic and resin fractions are retained in packed bed 615 by the stationary phase bed (i.e., the gel).

The saturates are routed to flowthrough optical cell 617, such that at 305 the spectrometer 619 measures the optical density of the saturates at a predetermined wavelength, transmitting the data to computer system 145. The saturates also pass through refractometer 660 where the refractive index is measured and transmitted to computer system 145.

During elution of the saturates, at 307 both UV-Vis data and refractive index (RI) data are recorded; however, the saturates fraction is colorless and is measured by refractive index. Nevertheless, the UV-Vis data during the saturates elution can be used for quality control to ensure that aromatics and resins are being sufficiently retained and are not breaking through into the saturates fraction. The eluted fluid from the packed bed 615 is collected in the saturates reservoir 622A for optional subsequent mass (gravimetric) measurement. The volume of heptane required for the elution of the saturates is determined by observing the optical signal (FIG. 4) and ensuring it reaches a stable plateau. It can be determined that the saturate fraction has been generally completely eluted when the refractive index drops to a near baseline level after being elevated for a period of time. For example, when it is determined that the optical signal has plateaued, the flow of heptane can be stopped by turning off pump 611.

Figure 4:
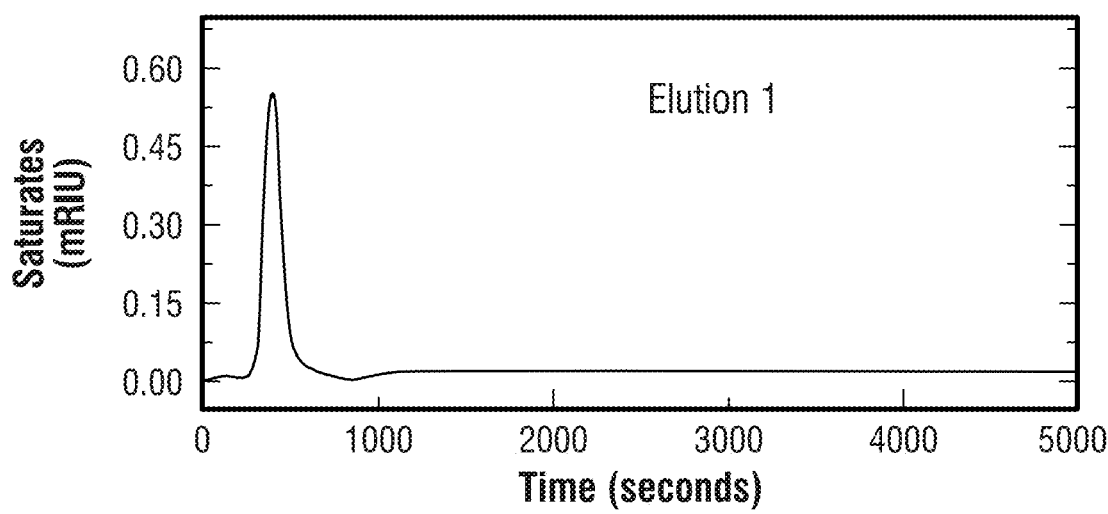
FIG. 4 is a graph showing a measurement of refractive index vs. time during an elution of saturates from a sample of permeate containing maltenes.

At 309 computer system 145 determines the peaks in the optical data shown in FIG. 4 and at 311 the data is filtered, such as by using a Savitzky-Golay filter. At 313 the maximum (peak) and thresholds of the refractive index curve are determined. At 315 a baseline of the refractive index curve is determined as a line connecting the curve between the thresholds. At 317 an area (As) under the refractive index curve bounded by the thresholds and the baseline is determined by integrating the curve to the baseline. The area $A_S$ may be determined automatically by a software program that employs peak edge detection and baseline correction. The area $A_S$ represents the total concentration of the saturate fraction, as will be discussed in greater detail below.

After the saturates have been eluted from the packed bed 615, at 321 valve 613 is set so that second solvent reservoir 607 is in fluid communication with pump 611 and valve 620 is set so that the aromatics reservoir 622B is in fluid communication with optical cell 617. At 321 pump 611 introduces the second solvent from second solvent reservoir 607 into the packed bed 615 to elute the aromatics of the maltenes portion. The eluent used to remove aromatics can be tuned for different types of stationary phase, and in the embodiment of FIGS. 1 and 3, a pre-mixed solution of 90% n-heptane and 10% toluene volume-to-volume is flowed through the column at 2.5 ml/minute.

During the aromatics elution, at 323 the eluted aromatics are routed to flowthrough optical cell 617, such that at 323 the spectrometer 619 measures the optical density of the aromatics at a predetermined wavelength, transmitting the data to computer system 145. At 325 UV-Vis optical absorbance data is recorded and the eluent is collected in the aromatics fraction bottle 622B. The volume required for the elution of the aromatics is determined by observing the optical signal and ensuring it reaches a stable plateau, as shown in FIG. 6, at which time the pump 611 can be turned off.

Figure 6:
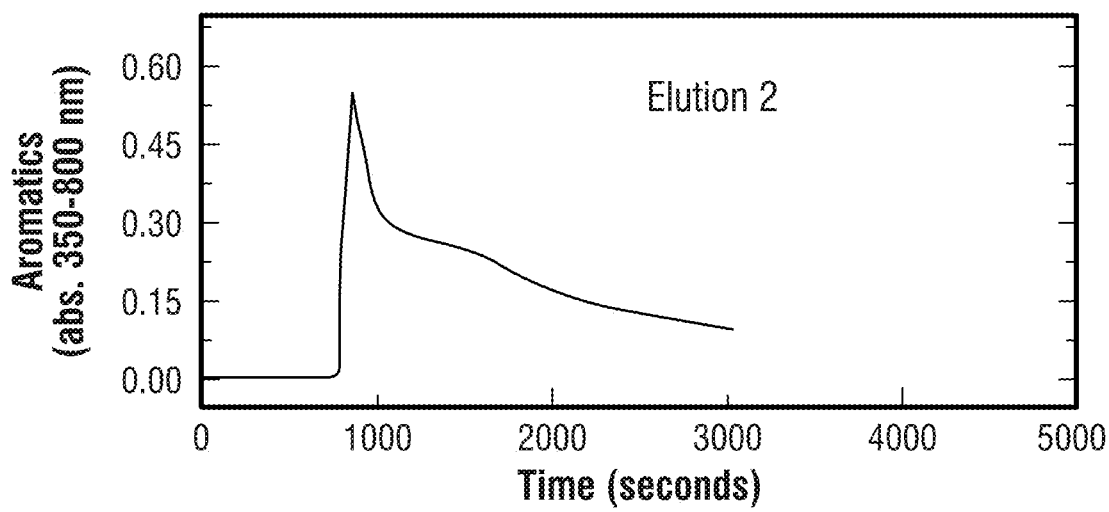
FIG. 6 is a graph showing a measurement of optical density vs. time during an elution of aromatics from a sample of permeate containing maltenes.

At 327 the computer system 145 determines the peaks in the optical density data shown in FIG. 6 and at 329 the data is filtered, such as by using a Savitzky-Golay filter. At 331 the maximum (peak) and thresholds of the optical density curve are determined. At 333 a baseline of the optical density curve is determined as a line connecting the curve between the thresholds. At 335 an area (AA) under the optical density curve bounded by the thresholds and the baseline is determined by integrating the curve to the baseline. The area AA may be determined automatically by a software program that employs peak edge detection and baseline correction. The area AA represents the total concentration of the aromatic fraction, as will be discussed in greater detail below.

Finally, after the aromatics have been eluted from packed bed 615, the resins fraction of the crude oil is extracted from packed bed 615 by eluting with a series of solvents, each solvent in the series increasing in polarity over time. In the embodiment shown in FIG. 1, two solvents are used to provide a controlled release of resins from the maltenes in packed bed 615. A series of solvents are employed so that the recorded optical density signal does not exceed the limit of the spectrometer 619 to preserve data quality. However, in at least one embodiment where there is no possibility of exceeding the limit of the spectrometer 619, a single elution with a resin-eluting solvent can be performed instead of a series of elutions. At 340 valve 613 is set so that the third solvent reservoir 609 is in fluid communication with pump 611 and the valve 620 is set so that the resins reservoir 622C is in fluid communication with optical cell 617. At 340 the pump 611 introduces the third solvent (a pre-mixed slightly polar solution of 2% isopropyl alcohol and 98% trichloromethane) from the third solvent reservoir 609 into the packed bed 615 to elute the resins of the maltenes portion. At 343 the resins eluted using the third solvent are routed to the flowthrough optical cell 617, such that spectrometer 619 measures the optical density of the resins from the first resin elution at a predetermined wavelength, transmitting the data to the computer system 145 where the optical density is recorded at 345.

At 347 the pump 611 introduces the fourth solvent (a pre-mixed slightly polar solution of 50% isopropyl alcohol and 50% trichloromethane) from the fourth solvent reservoir 610 into the packed bed 615 to elute the remaining resins of the maltenes portion. At 349 the resins eluted using the fourth solvent are routed to the flowthrough cell 617 such that the spectrometer 619 measures the optical density of the resins at a predetermined wavelength, transmitting the data to the computer system 145 where the data is recorded at 351. The optical density data is collected for the duration of both resin elutions of the series, performed at 2.5 ml/minute, and both eluents are stored in the resins reservoir 622C. The volumes of the third and fourth solvents required for each elution are determined by observing the optical signal (FIG. 8) and ensuring it reaches a stable plateau.

Figure 8:
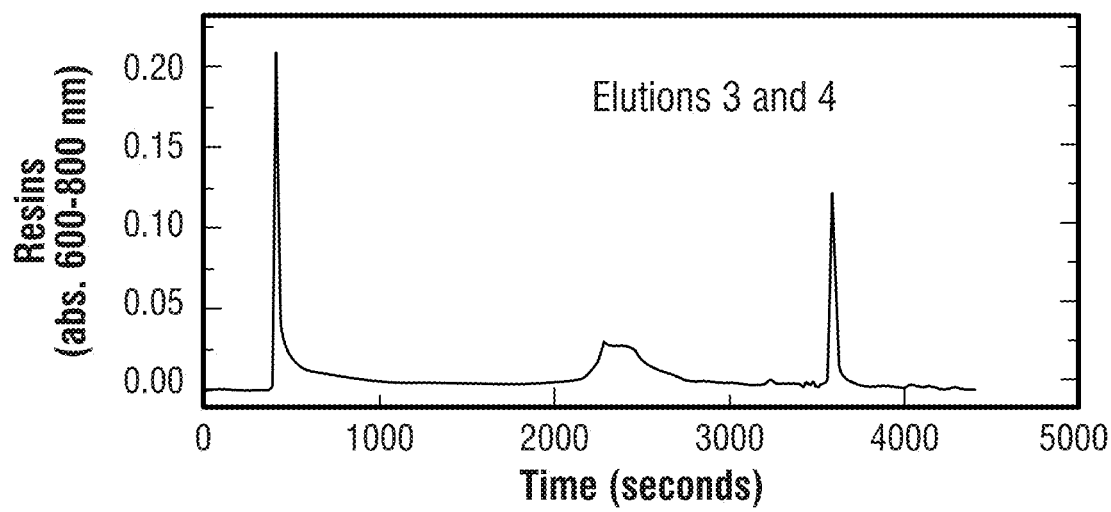
FIG. 8 is a graph showing a measurement of optical density vs. time during an elution of resins from a sample of permeate containing maltenes.

At 353 the computer system 145 determines the peaks in the optical data shown in FIG. 8 and at 355 the data is filtered, such as by using a Savitzky-Golay filter. At 357 the maximums (peaks) and thresholds of the optical density curve are determined. At 359 baselines of the optical density curve are determined as lines connecting the portions of the curves between the thresholds under the respective peaks corresponding to each of the two resin elutions. At 361 an area (AR) under the optical density curve bounded by the thresholds and the baselines is determined by integrating the curve to the baselines. The area AR may be determined automatically by a software program that employs peak edge detection and baseline correction. The area AR represents the total concentration of the resin fraction, as will be discussed in greater detail below.

At 363 the mass fractions of saturates ($m_S$), aromatics ($m_A$), and resins ($m_R$) are calculated from the following relationships:

$$m_s = RF_s * A_s + k_s, \quad (4)$$

$$m_A = RF_A * A_A + k_A, \text{ and} \quad (5)$$

$$m_R = RF_R * A_R + k_R. \quad (6)$$

where $RF_S$ refers to a response factor and $k_s$ refers to a calibration constant, both of which are from calibration data obtained from known sources of saturates derived from crude oil samples;

$RF_A$ refers to a response factor and $k_A$ refers to a calibration constant, both of which are from calibration data obtained from known sources of aromatics derived from crude oil samples; and $RF_R$ refers to a response factor and $k_R$ refers to a calibration constant, both of which are from calibration data obtained from known sources of resins derived from crude oil samples.

Figure 5:
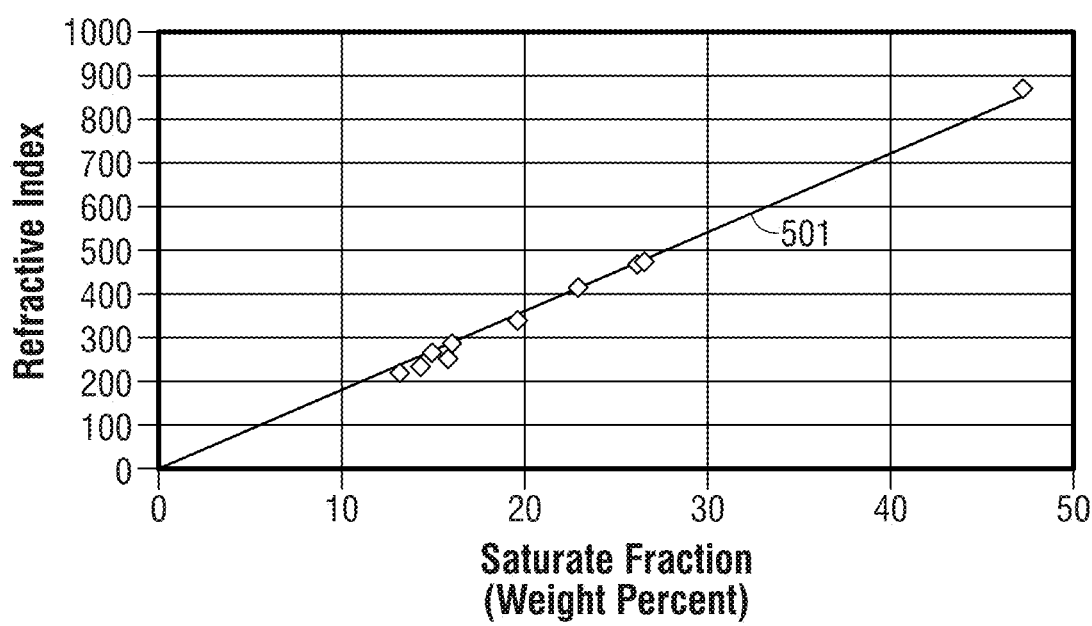
FIG. 5 is a calibration curve for determining linear coefficients to correlate the optical data in FIG. 4 with a saturate mass fraction.

To generate the response factor $RF_s$ and the calibration constant $k_s$, the saturate fraction is collected while monitoring the optical density at a wavelength of about 285 nanometers. The refractive index is measured over time as the saturate fraction is eluted. FIG. 5 depicts a graphical representation of correlations between the saturate fractions from a variety of crude oil maltenes and the integral over the refractive index curve portion, for example, like that obtained from 317. Line 501 in FIG. 5 represents a best-fit linear curve based upon the data points, illustrating that the optical techniques of the present disclosure are sufficiently accurate for a wide variety of crude oil types.

Figure 7:
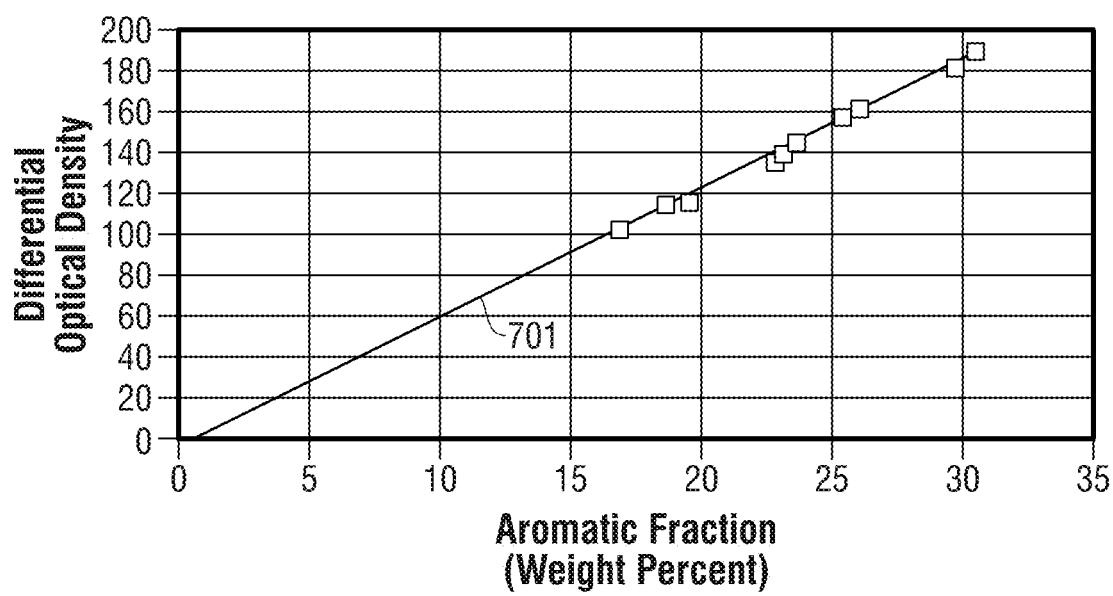
FIG. 7 is a calibration curve for determining linear coefficients to correlate the optical data in FIG. 6 with an aromatic mass fraction.

To generate the response factor $RF_A$ and the calibration constant $k_A$, the aromatic fraction is collected while monitoring the optical density at a wavelength of about 350 nanometers. The optical density is measured over time as the aromatic fraction is eluted. FIG. 7 depicts a graphical representation of correlations between the aromatic fractions from a variety of crude oil maltenes and the integral over the differential optical density curve portion, for example, like that calculated at 335, for the variety of crude oil maltenes. Line 701 in FIG. 7 represents a best-fit linear curve based upon the data points, illustrating that the optical techniques of the present disclosure are sufficiently accurate for a wide variety of crude oil types.

Figure 9:
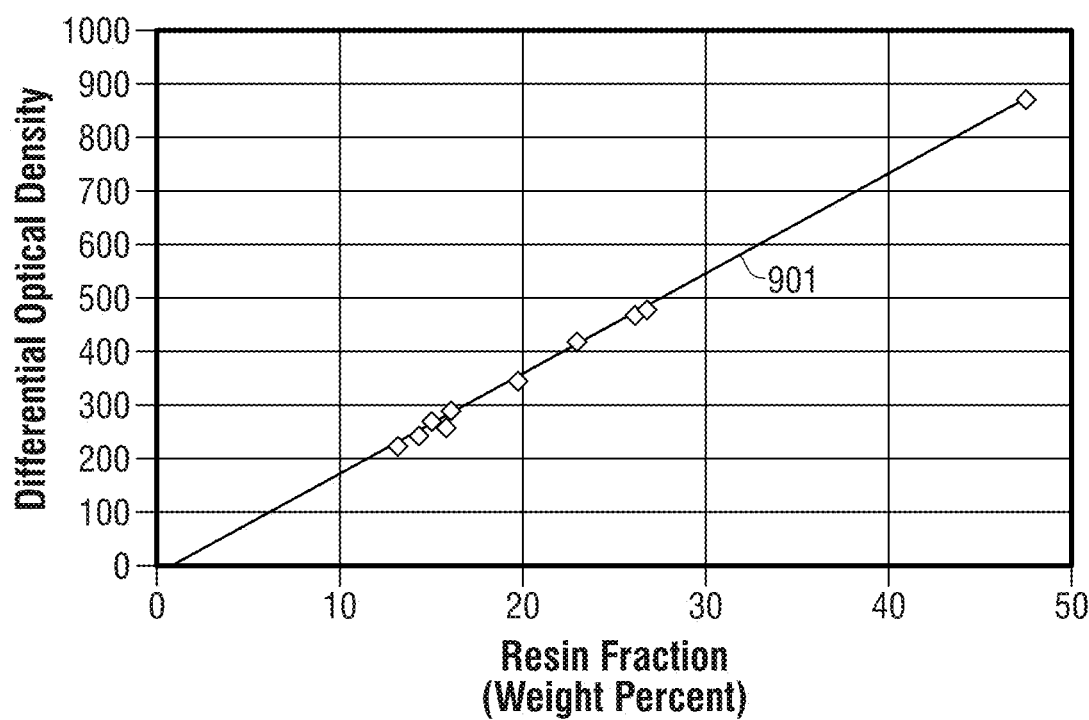
FIG. 9 is a calibration curve for determining linear coefficients to correlate the optical data in FIG. 8 with a resin mass fraction.

To generate the response factor $RF_R$ and the calibration constant $k_R$, the resin fraction is collected while monitoring the optical density at a wavelength of about 600 nanometers. The optical density is measured over time as the resin fraction is eluted. FIG. 9 depicts a graphical representation of correlations between the resin fractions from a variety of crude oil maltenes and the integral over the differential optical density curve portion, for example, like that at 361, for the variety of crude oil maltenes. Line 901 in FIG. 9 represents a best-fit linear curve based upon the data points, illustrating that the optical techniques of the present disclosure are sufficiently accurate for a wide variety of crude oil types.

Once all of the mass fractions ($m_S$, $m_A$, $m_R$) are calculated, a sum of predicted masses can be calculated at 365. At 367 predicted mass percentages of the maltenes are calculated for the saturates ($m_S$ %), aromatics ($m_A$ %), and resins ($m_R$ %) as follows:

$$m_S\% = m_S/M_T, \quad (7)$$

$$m_A\% = M_A/M_T, \text{ and} \quad (8)$$

$$m_R\% = m_R/m_T. \quad (9)$$

At 369 the mass percentages can be normalized to asphaltenes to calculate the saturate mass concentration ($M_S$ %), aromatic mass concentration ($M_A$ %), and resin mass concentration ($M_R$ %) as follows:

$$M_S\% = (m_S\%)*(1-M_{Asph}), \quad (10)$$

$$M_A\% = (m_A\%)*(1-M_{Asph}), \text{ and} \quad (11)$$

$$M_R\% = (m_R\%)*(1-M_{Asph}) \quad (12)$$

where $M_{Asph}$ is acquired according to the method described in U.S. Pat. No. 8,269,961.

Figure 10:
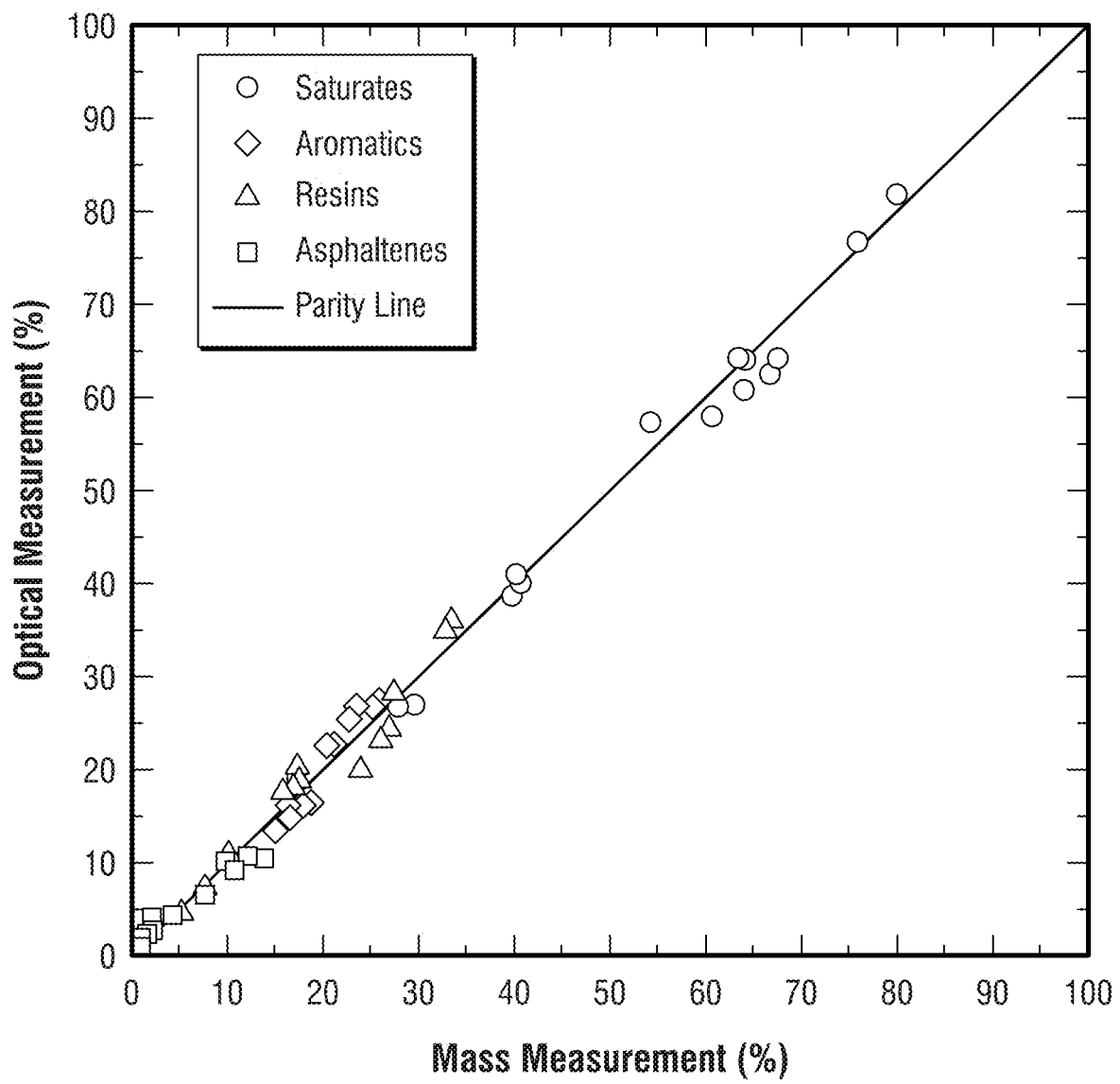
FIG. 10 is a graph showing a comparison of weight measurements using conventional wet chemistry and the percentages from the optical correlation data.
Figure 11:
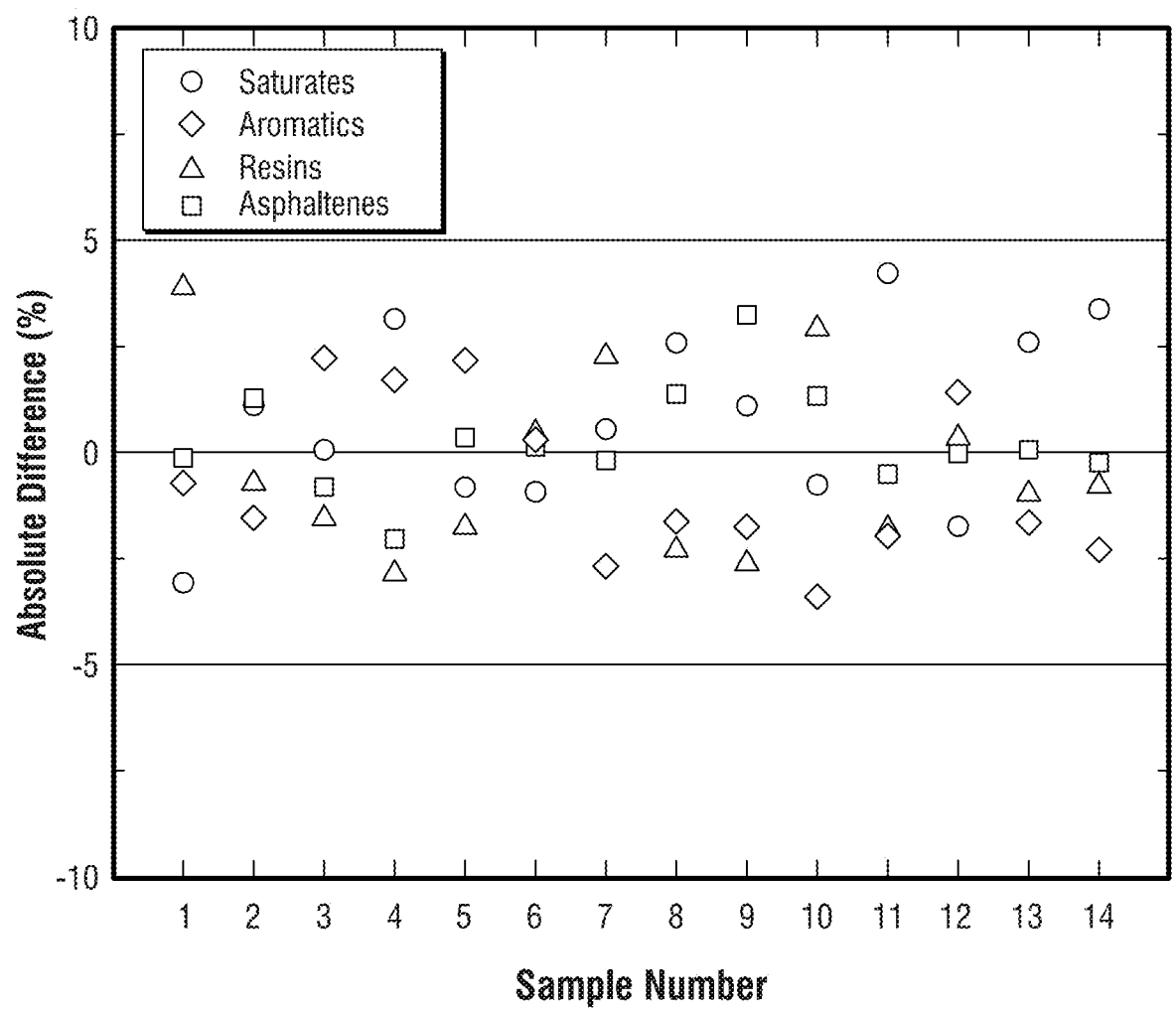
FIG. 11 is a graph showing absolute differences from correlation data.

The collected eluents in collection reservoirs 622A, 622B, and 622C can optionally be concentrated using a rotary evaporator and the respective masses of saturates, aromatics, and resins weighed. The fractional masses can be plotted versus their corresponding optical signals. The linear correlation between mass and optical signal area for all three fractions generates response factors (RF) and constants (k) that are used to calculate composition percentages. Normalized optical fraction percentages are plotted versus normalized mass fraction percentages, as shown in FIG. 10. The absolute difference between the two techniques by fraction and by sample is shown in FIG. 11. The maximum absolute deviations are 4.2% for saturates, 3.4% for aromatics, 3.9% for resins and 3.2% for asphaltenes. The results show that it is possible to use combinations of optical spectroscopy techniques, namely UV-Vis absorbance and refractive index, to rapidly determine SARA fraction percentages. Masses were weighed in the initial experiments to establish universal correlation factors. In future runs, masses need not be weighed and optical areas can be used to determine fraction percentages. The total runtime for the optical measurement was on the order of hours as compared with the days associated with gravimetric measurement. The technique reported is miniaturized utilizing lower solvent volumes and is automated—providing a complete and repeatable SARA analysis with minimal user bias.

There have been described and illustrated herein several embodiments of an automated test apparatus and method that characterizes SARA fractions of a hydrocarbon sample that employs microfluidics. While particular embodiments have been described herein with reference to particular means, materials, and embodiments, it is not intended to be limited to the particulars described herein; rather it extends to all functionally equivalent structures, methods and uses, such as are within the scope of the appended claims.

What is claimed is:

1. A system for obtaining saturate, aromatic, resin, and asphaltene (SARA) fractions of a hydrocarbon sample, comprising:
    a microfluidic portion constructed to receive a hydrocarbon sample, separate and analyze asphaltenes from the hydrocarbon sample, and discharge a permeate containing maltenes; and
    a chromatographic portion coupled to the microfluidic portion and constructed to receive the permeate therefrom and separate and analyze saturate, aromatic, and resin fractions in the permeate,
    wherein the chromatographic portion includes a refractometer,
    wherein the chromatographic portion further includes a selection valve coupled to at least one saturate reservoir, at least one aromatic reservoir, and at least one resin reservoir,
    wherein the selection valve is configured to allow the separated saturate, aromatic, and resin fractions to flow to the at least one saturate reservoir, the at least one aromatic reservoir, and the at least one resin reservoir, respectively, and wherein the refractometer is fluidly coupled between the selection valve and the at least one saturate reservoir.

2. A system according to claim 1, wherein the microfluidic portion includes at least one microfluidic chip and the chromatographic portion includes at least one chromatographic column.

3. A system according to claim 2, wherein:

the at least one microfluidic chip comprises first and second inlet ports that are fluidly coupled to a mixer section;

wherein the first inlet port is fluidly coupled to a supply of a solvent fluid and the second inlet port is fluidly coupled to a supply of a titrant fluid; and wherein the first inlet port is configured to supply the hydrocarbon sample to the mixer section with the solvent fluid.

4. A system according to claim 3, wherein the at least one microfluidic chip comprises a reactor section fluidly coupled downstream from the mixer section, and a membrane filter section fluidly coupled downstream from the reactor section, wherein the membrane filter section leads to both a waste port and an outlet port.

5. A system according to claim 4, wherein the microfluidic portion includes a first optical cell fluidly coupled to receive filtered fluid from the membrane filter section, and a first spectrometer optically coupled to the first optical cell constructed to obtain absorbance data from the fluid passing through the first optical cell.

6. A system according to claim 5, wherein the chromatographic portion includes a second optical cell fluidly coupled to receive fluid from the at least one chromatographic column, and a second spectrometer optically coupled to the second optical cell constructed to obtain optical properties from the fluid passing through the second optical cell.

7. A system according to claim 6, wherein the chromatographic portion includes a pump and a valve coupled to a plurality of reservoirs of titrants, the pump and valve constructed to sequentially introduce the titrants into the at least one chromatographic column to sequentially separate saturates, aromatics, and resins from the permeate.

* * * * *